United States Patent

Ghajar et al.

[11] Patent Number: 5,180,387
[45] Date of Patent: Jan. 19, 1993

[54] ANGLED HOLE VENTRICULAR CATHETER WITH NON-CIRCULAR BORE

[75] Inventors: Jamshid B. G. Ghajar; Robert J. Hariri; Fathali G. Ghadjar, all of New York, N.Y.

[73] Assignee: Neurodynamics, Inc., New York, N.Y.

[21] Appl. No.: 266,451

[22] Filed: Nov. 2, 1988

Related U.S. Application Data

[63] Continuation-in-part of Ser. No. 98,097, Sep. 17, 1987, Pat. No. 4,784,638.

[51] Int. Cl.$^5$ .............................................. A61M 31/00
[52] U.S. Cl. ..................................... 604/266; 604/282
[58] Field of Search ................ 604/280, 282, 264, 266

[56] References Cited

U.S. PATENT DOCUMENTS

| | | | |
|---|---|---|---|
| 1,596,754 | 10/1923 | Moschelle | 604/232 |
| 2,393,003 | 1/1946 | Smith | 604/170 |
| 2,972,779 | 2/1961 | Cowley | 604/280 |
| 3,006,524 | 10/1961 | Laws | 604/275 |
| 3,017,887 | 1/1962 | Heyer . | |
| 3,020,913 | 2/1962 | Heyer | 604/9 |
| 3,073,310 | 1/1963 | Mocarski . | |
| 3,136,316 | 6/1964 | Beall | 604/268 |
| 3,605,750 | 4/1969 | Sheridan et al. | 604/280 |
| 3,605,750 | 9/1971 | Sheridan et al. | 604/280 |
| 3,608,555 | 9/1971 | Greyson | 604/280 |
| 3,645,955 | 2/1972 | Flynn | 604/280 |
| 3,805,561 | 5/1974 | Cami | 604/247 |
| 3,825,001 | 7/1974 | Bennet et al. . | |
| 3,828,767 | 8/1974 | Spiroff . | |
| 3,885,561 | 5/1975 | Cami | 604/247 |
| 4,139,012 | 2/1979 | Zahorsky | 604/268 |
| 4,246,936 | 1/1981 | Luz | 138/103 |
| 4,257,422 | 3/1981 | Duncan | 604/282 |
| 4,391,276 | 7/1983 | Lazarus et al. | 604/266 |
| 4,406,656 | 9/1983 | Hattler et al. | 604/282 |
| 4,465,482 | 8/1984 | Tittel | 604/280 |
| 4,500,313 | 2/1985 | Young | 604/280 |
| 4,559,046 | 12/1985 | Groshong et al. | 604/282 |
| 4,613,324 | 9/1986 | Ghajar | 604/49 |
| 4,632,668 | 12/1986 | Wilson, Jr. et al. . | |
| 4,655,745 | 4/1987 | Corbett . | |
| 4,668,221 | 5/1987 | Luther | 604/164 |
| 4,681,570 | 7/1987 | Dalton | 604/282 |
| 4,701,166 | 10/1987 | Groshong et al. | 604/8 |
| 4,737,152 | 4/1988 | Alchas | 604/9 |
| 4,769,005 | 9/1988 | Ginsburg et al. | 604/53 |
| 4,784,638 | 11/1988 | Ghajar et al. | 604/9 |
| 4,784,651 | 11/1988 | Hickey | 604/282 |
| 4,823,805 | 4/1989 | Wojcik | 604/282 |
| 4,894,053 | 1/1990 | Reddiek | 604/229 |

OTHER PUBLICATIONS

Ghajar, A. Guide For Ventricular Catheter Placement, J. Neurosurg. 63:985-986 (1985) and Instruction Manual for described device.

Cooper, the Neurosurgical Alleviation of Parkensonism, Chemopallidectomy p. 83 (1956).

Kandall, A Trephine Needle for Vertebral Body Biopsy, the Lancet, Feb. 27, 1960, p. 474.

*Primary Examiner*—C. Fred Rosenbaum
*Attorney, Agent, or Firm*—Pennie & Edmonds

[57] ABSTRACT

A catheter for placement into the ventricular system of the brain or any other member or cavity of the body of a subject comprising a flexible elongated body having a non-circular bore, a wall thickness sufficient to contain and transport fluid therein, a forward end and tip for insertion into the ventricular system of the brain of a subject, and a plurality of spaced apertures located in the forward end of the body spaced from the tip. The apertures are configured and positioned to minimize abrasion of brain tissue upon insertion of the catheter and to prevent tissue from growing into the catheter apertures, thereby providing improved flow of fluid into or from said ventricular system. The non-circular bore, preferably triangular, provides increased structural integrity and increased effective flow through the catheter compared to those having a circular bore. Also methods of using such catheters are disclosed herein.

17 Claims, 1 Drawing Sheet

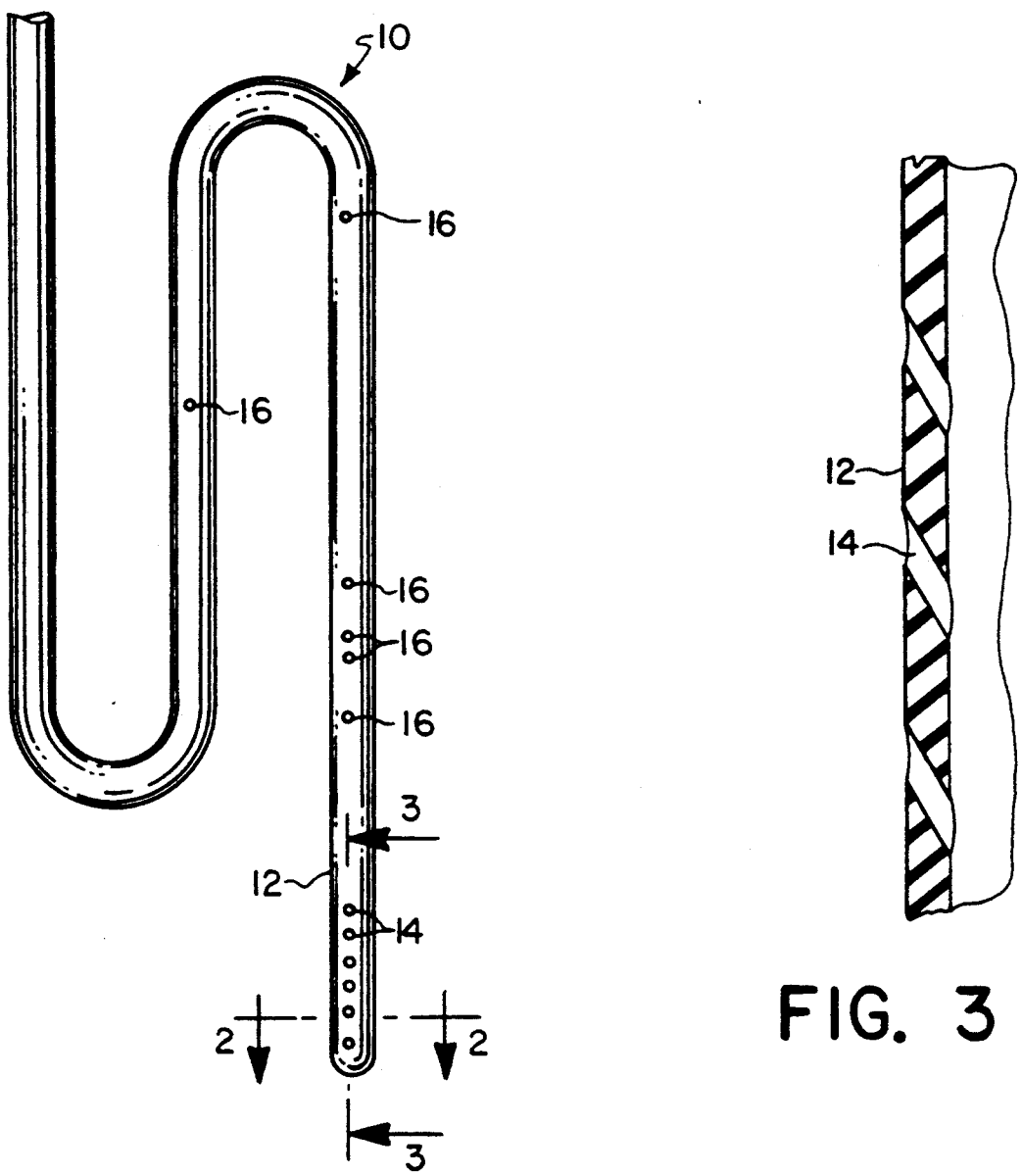
FIG. 1
FIG. 3
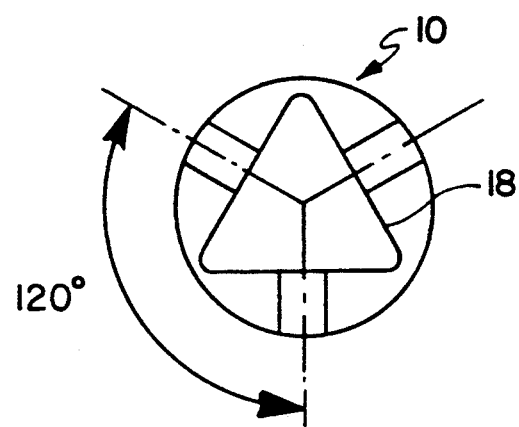
FIG. 2

ANGLED HOLE VENTRICULAR CATHETER WITH NON-CIRCULAR BORE

CROSS REFERENCE TO RELATED APPLICATIONS

This application is a continuation-in-part of application Ser. No. 098,097 filed Sep. 17, 1987 now U.S. Pat. No. 4,784,638.

TECHNICAL FIELD

The present invention relates to a catheter having specifically angled apertures and a non-circular bore which facilitate access to or drainage of fluid within or from a host.

BACKGROUND OF THE INVENTION

The four ventricles of the human brain are interconnected cavities that produce and circulate cerebral spinal fluid (CSF). Procedures involving ventriculostomy, i.e., placement of a catheter into the ventricular system of the brain, form a major part of a neurosurgeon's clinical practice. General areas of application of ventricular catheter placement include intracranial pressure monitoring (ICP), draining or shunting of CSF and the instillation of pharmacological therapeutic agents.

CSF drainage is essential for patients with congenital or acquired hydrocephalus. CSF drainage, which can only be performed with an intraventricular catheter, is a life-preserving procedure, because it can immediately reduce intracranial pressure. The ventricular catheter, used to drain CSF, is connected to a peripheral subcutaneous drainage system, i.e., to the peritoneal cavity or systemic circulation via the heart or in the case of ICP to an external drainage collection system. Standard procedures for ventricular catherization are disclosed in the textbook literature. See, for example, Neurosurgery, edited by Robert H. Wilkins and Setti S. Rengachary, Section A, Chapter 13, Techniques of Ventricular Puncture (McGraw Hill 1984).

The most frequently chosen site for ventricular catheterization is coronal. In most cases, a catheter is inserted in the anterior horn of the lateral ventricle through an orifice or burr hole drilled just anterior to the coronal suture in the midpupillary line of the cranium, i.e., in the frontal bone over the ventricle. This is known in the field as Kocher's point. The burr hole, only slightly larger than the diameter of the selected catheter to insure a snug fit and provide a seal against CSF leakage, is placed approximately 1 cm anterior to the coronal suture, approximately 10 to 12 cm above the nasion, and approximately 2 to 3 cm from the midline over the nondominant hemisphere. After the burr hole is made, the dura and underlying pia-arachnoid are opened and coagulated, for example, with a fine-tipped blade after cauterizing the dural surface.

The lateral ventricles of the human brain form an arc parallel to the arc of the cranium, i.e., the contour of the lateral ventricles parallels the arc of the surface of the skull. Thus, a catheter guided perpendicular to the cranial surface at the point of entry into the cranium will enter the ventricular system. Specifically, any line penetrating a burr hole in the surface of the skull at a 90° angle also bisects the lateral ventricle.

A more recently developed procedure to ensure correct catheter placement is disclosed in U.S. Pat. No. 4,613,324. The apparatus comprises a guide assembly which, when positioned over an orifice drilled in the cranium above the anterior horn of the lateral ventricle, guides a catheter and obturator through the orifice and into the lateral ventricle at an angle normal to an imaginary plane formed by a tangent to the cranium at the orifice, while the corresponding method comprises providing an orifice in the cranium just anterior to a coronal suture in a midpupillary line of the cranium and inserting a ventricular catheter containing an obturator through the orifice towards a lateral ventricle, wherein the catheter containing the obturator is guided through the orifice, by means of a novel guide assembly, at an angle normal to an imaginary plane formed by a tangent to the cranium at the orifice.

A wide variety of catheters are known in the prior art for the purpose of penetrating the ventricular cavity. Such catheters are typically in the form of a hollow tube with a circular bore which is provided with a plurality of apertures at the ventricular or inflow end to permit the passage of CSF from the brain into the catheter and thence to the bloodstream or peritoneal cavity of the patient or to an external drainage system. However, malfunctions frequently occur with such a catheter due to the blockage of the apertures in the inflow end of the catheter. Such blockage is usually caused by the growth of choroid plexus or ependymal tissue within the ventricle into the apertures in the inflow end of the catheter. This tissue may block the apertures in the inflow end of the catheter in a relatively short period of time after the catheter has been inserted into the ventricle thereby rendering the cathether inoperative in relieving excess pressure due to the build-up of CSF within the ventricle. Furthermore, prior art catheter apertures are cut perpendicular to the length of the catheter, thus causing abrasion of brain tissue when the catheter is inserted.

The likelihood of ventricular catheter malfunction by aperture plugging with brain tissue can be lessened by angling the aperture holes in the wall of the catheter such that there is "no see through" flow from the outside to the inside of the lumen. Also, by positioning the rows of apertures 120° apart there is essentially no chance for direct ingrowth of ventricular tissue therethrough. In addition, the apertures are angled away from the direction of the insertion of the catheter into the brain thus lessening the chance of brain abrasion. Further, by slightly stretching the catheter by means of the stylet (which is integral to the catheter and used for placement of it into the brain) the holes will close so that no opening will be visible during the placement thereof, with the holes re-opening after the tension on the catheter is relieved by removal of the stylet.

A catheter may also malfunction by kinking due to insufficient structural rigidity. Kinking may cause blockages or ineffective flow paths within the catheter, thereby rendering it inoperative in relieving excess pressure due to the build-up of CSF within the ventricle. In addition, kinking may cause the catheter to wander off course and make the insertion more difficult for the neurosurgeon and more harmful to the patient. The likelihood of the catheter kinking can be lessened by using a non-circular bore which will increase structural rigidity and strength.

As such, it would be desirable to provide a catheter which overcomes the problems of previously devised ventricular catheters which are emplaceable within a ventricle of a human brain to control the flow of excess fluids to or from the brain. The present invention provides a simple solution which resolves the problems of prior art catheters in a novel and unexpected manner.

SUMMARY OF THE INVENTION

The present invention relates to a catheter for placement into a host for accessing fluid therein, preferably for insertion into the ventricular system of the brain of a subject to access CSF. This catheter comprises a flexible elongated body with a non-circular bore having a wall thickness sufficient to contain and transport fluid therein. The body has a forward end and tip for insertion into the ventricular system and a plurality of spaced apertures located in the forward end of the body spaced from the tip. Each of the apertures extends through the wall thickness at an angle such that a portion of the wall thickness is visible when viewing the aperture perpendicular to the axis of the body. This arrangement facilitates closure of the apertures by slightly stretching the body with a placement stylet to minimize abrasion of brain tissue upon insertion of the catheter. This arrangement also helps prevent choroid plexus tissue from growing into the catheter apertures, thereby providing improved flow of fluid into or from the ventricular system.

Preferably, each of the apertures extends through the wall thickness at an angle of about 35° with respect to the longitudinal axis of the body, and a plurality of apertures are aligned in a number of rows. Also, rows of these apertures are spaced 120° apart around the circumference of the body for maximizing the structural integrity of the catheter forward end.

The body of the catheter is provided with a bore to transport fluids into and out of the brain. In order to increase the structural integrity and the effective flow area of the catheter, as compared to a circular bore catheter, a bore in the form of a polygon, and preferably, in the form of an equilateral triangle is employed.

If desired, the forward end of the body can be made of a radioopaque material at least in the area surrounding the apertures to facilitate monitoring of catheter placement. The body may include means to indicate the depth of penetration of the catheter forward end to assist in proper placement thereof. These depth penetration indication means may be markings of a radioopaque material to facilitate monitoring of the placement of the catheter.

The invention also relates to method of accessing CSF in a ventricle within a human cranium which comprises drilling an orifice in the cranium just anterior to a coronal suture in a midpupillary line of the cranium, and guiding a catheter through the orifice by means of a guide assembly in a direction perpendicular to an imaginary plane defined by a tangent to the cranium at the orifice. The catheter thus accurately penetrates the ventricle on the first insertion with minimal abrasion of brain tissue. The catheter, described above, i.e., one having the appropriate positioning and configuration of apertures to minimize ventricular tissue growth thereinto, is preferred so that increased flow of fluid to or from the ventricle is obtained.

The catheter of this method utilizes a guide assembly comprising tubular means and support means for the tubular means. Therefore, the method further comprises placing the support means so as to rest unsecured on the human cranium in surrounding spaced relation to the orifice, and guiding the catheter through the tubular means, into the orifice and into the ventricle. The support means and tubular means are related to each other such that the catheter is guided through the orifice by the tubular means in a direction perpendicular to an imaginary plane defined by a tangent to the cranium of the orifice, independent of the orifice. To accomplish this, the tubular means is supported through a support means comprising a plurality of legs of equal length.

Also, this method further comprises inserting a removable insert within the tubular means to reduce the diameter thereof for receiving the catheter. A stylet may be utilized to assist in the insertion of the catheter in a manner such that the catheter is stretched so as to flatten the apertures to further reduce abrasion of brain tissue upon insertion therein. In a preferred arrangement, the catheter body includes means for indicating the depth of penetration of the catheter forward end so that the method further comprises inserting the catheter to a predetermined depth into the ventricle. The indicating means may be radioopaque markings so that the placement of the catheter in the ventricle can be monitored.

BRIEF DESCRIPTION OF THE DRAWINGS

Preferred embodiments of the invention are described hereinbelow with reference to the drawing figures wherein:

FIG. 1 is a perspective view of a catheter according to the invention;

FIG. 2 is a cross-sectional view taken along line 2—2 of FIG. 1; and

FIG. 3 is a cross-sectional view taken along line 3—3 of FIG. 1;

DETAILED DESCRIPTION OF THE PREFERRED EMBODIMENTS

Referring initially to FIG. 1 there is illustrated catheter 10 which is intended for insertion into a ventricle of the human brain for access to or drainage of CSF such as; for example, would be necessary to drain excess CSF during treatment of hydrocephalus. Since the present invention is primarily concerned with the forward or insertion end of the catheter, a detailed description of the opposite or out flow end of the catheter is not provided as such details are well known in the relevant surgical art.

This catheter 10 is a flexible, hollow, elongated member having a sufficient wall thickness for the containment and or transport of fluids therein and therethrough. The forward end 12 of the catheter includes a plurality of apparatus 14 for access to CSF in the ventricle of the brain. By "access" what is meant is contact of CSF for removal or drainage from the brain or, conversely, to enable medicaments or other fluids to be directed or delivered into the brain from the catheter through the apertures 14. These apertures 14 are positioned and configured in a predetermined manner so as to allow for a better and more continuous flow of fluids in and through the catheter with less chance of plugging the holes due to ingrowth of a brain tissue when the catheter is placed in the ventricle. Further, the design of the holes enables the catheter placement to be made in an improved, easier manner while causing less abrasion damage to tissue during insertion of the catheter.

As shown in FIG. 2, the catheter 10 is designed with a bore in the shape of an equilateral triangle 18. This shape is preferred over a circular shape because it provides 1.7 times the effective flow area while providing additional structural integrity. Further, this shape can easily be partitioned to allow the formation of secondary lumens to run other implements into the ventricle, within the main lumen while maintaining sufficient flow area.

As shown in FIGS. 2 and 3, the catheter 10 is designed with 3 sets of holes set 120° apart, the centers of which coincide with the midpoint of each side of the triangular bore 18. These holes are cut at an angle into the wall of the catheter such that the angle of the cut is measured along the longitudinal axis of the catheter in the direction of movement of the catheter when it is inserted into the ventricle. Further, the diameter of each hole in the catheter is proportional to the thickness of the catheter wall so that, as best illustrated in FIG. 3, there is no direct linear visual access to the interior of the catheter when the holes are viewed perpendicular to the longitudinal axis of the catheter.

By preparing the holes in this manner, abrasion of brain tissue is minimized upon insertion of the catheter into the ventricle, so less brain tissue is destroyed as a direct result of such decreased abrasion. Further, by stretching the catheter slightly, the holes in the catheter are closed thus preventing such tissue as may come in contact with the catheter from entering the lumen upon insertion. The stretching of the catheter can easily be accomplished when a rigid placement stylet is used: the body of the catheter being slightly pulled back from the insertion end while the stylet is held, thus allowing the holes to be somewhat flattened. This lack of direct access to the inside of the catheter prevents the growth of brain cells or tissue therein, thus resolving one of the major causes of plugging and malfunction of prior art catheters which utilize 90° or perpendicular apertures. The 120° peripheral offset for each set of holes further minimizes the possibility that choroid plexus or brain cell growth will extend across the inner diameter of the catheter even if such growth does penetrate into one or more of the holes.

Although the holes are advantageously shown as being cut at an angle of 35° with respect to the longitudinal axis of the catheter, it is to be noted that other angles can also be used in this invention provided that direct access to the inside of the catheter is prevented. These other angles would be somewhat dependent upon wall thickness of the catheter, since heavier wall thicknesses would allow a greater range of angles while still preventing direct access into the catheter interior. Suitable angles for any specific catheter construction can be determined from the relationship $d = t/\tan\theta$, where d is the diameter of the aperture, t is the wall thickness of the catheter, and $\theta$ is the angle between the cut of the aperture and the longitudinal axis of the catheter body. As shown by the relationship of these variables, the diameter of the aperture must be less than or equal to the wall thickness of the catheter divided by the tangent of the angle. To calculate suitable angles for any particular aperture size and catheter wall thickness, the formula would be $\theta = \tan^{-1} t/d$, so that the tangent of the angle, $\theta$ is greater than the quotient of the thickness divided by the diameter.

To assist in the understanding of the invention, direct access is avoided when the diameter of the hole on the outside wall of the catheter does not overlap the diameter of the hole on the inner wall catheter when viewed in a line perpendicular to the wall of the catheter. Thus, it is possible to utilize angles other than 35° although 35° has been found to be particularly advantageous.

By placing the holes to avoid direct access to the inside of the catheter, it is possible to cut the holes larger in diameter than they would be if direct access was provided without weakening the structural integrity of the catheter. These larger holes allow for an increased flow of CSF into the catheter while also making it more difficult for any possible brain cell growth to plug the entire hole, compared to the relatively smaller diameter holes of prior art catheters which provide direct access into the body of the catheter.

The catheter of the invention can be inserted into the ventricle of the brain in any manner currently known, including "freehand" or with the use of a guide. To assist in the proper location and placement of the catheter, a plurality of markings 16 are provided along the length of the catheter body. These markings correspond to predetermined insertion lengths of the catheter and enables the surgeon to know precisely how far the tip of catheter is inserted into the ventricle By making these markings of a radioopaque material such as barium, the depth of placement of the catheter can easily be monitored by conventional techniques. Furthermore, if desired, the forward section of the catheter in the area around the apertures can also be made of a radioopaque material for viewing on various scanning equipment the precise placement of the forward end and tip of the catheter.

The improvements provided by the catheter of this invention are significant in that the physician does not require any guess work to determine the precise placement of the catheter in the patient's brain. Furthermore, when so placed, the catheter provides improved fluid delivery and/or removal with minimal disturbance of the surrounding brain cells while also discouraging brain tissue growth into the catheter apertures. As mentioned above, the catheter can be inserted in the brain in any manner commonly utilized. Rather than a "free hand" technique, it is advantageous to utilize a guide assembly to insure correct catheter placement.

One method of accessing the ventricle is by drilling a hole in the skull by using a manual twist drill and supporting guide. After drilling the hole, the drill guide can be converted to a catheter guide by use of an insert. This method and the apparatus associated therewith are disclosed in U.S. patent application Ser. No. 093,426, Sep. 4, 1987, the content of which is expressly incorporated herein by reference thereto.

Another preferred guide apparatus and method of insertion of a catheter into the ventricle is disclosed in U.S. Pat. No. 4,613,324, the disclosure of which is expressly incorporated herein by reference thereto. As shown in the patent, a stylet is used to assist in the insertion of the catheter. As noted above, the stylet can be used to stretch the present catheters so that the angled apertures can be flattened to minimize the abrasion of brain tissue during insertion. Also, this flattening operation slightly reduces the overall diameter of the catheter which further reduces such abrasion.

It is known for certain applications to utilize a second stylet for guiding the catheter into the ventricle. In prior art catheters, this second stylet is inserted into one of the apertures at the forward end of the catheter. Since those apertures are cut at 90° an unwieldy assembly is created. Any attempt to align the second stylet parallel to and adjacent the first stylet and catheter causes the tip to be somewhat bent, thus causing further difficulties in its insertion and penetration of the ventricle. The present invention significantly reduces and minimizes this problem since the angled holes are more receptive to the introduction of the second stylet in a compact orientation (i.e., in a "V" shape, rather than an "L" shape) which greatly enhances the manipulation of the catheter and stylets during placement in the ventricle.

Prior art catheters, as noted above, have four sets of holes oriented 90° apart along the circumference of the catheter. In addition to weakening the strength and structural integrity of the catheter in the tip area, holes on opposite sides of the catheter (i.e., those 180° apart) are made simultaneously by a punching tool. This results in holes on one side being larger in diameter than those on the opposite side. Therefore, two sets of holes are large and two are small. This non-uniformity affects CSF flow and the smaller holes can easily become blocked by brain tissue growth, thus causing reduced operation of those catheters.

The present invention resolves these problems by accurately and precisely placing three sets of uniform holes cut at the desired angle to the catheter body and spaced apart exactly by 120°. This results in increased flow through the holes, higher strength and integrity of the catheter body, and greater ease of insertion and placement of the catheter in the ventricle.

While it is apparent that the invention herein disclosed is well calculated to fulfill the objects above stated, it will be appreciated that numerous modifications and embodiments may be devised by those skilled in the art, and it is intended that the appended claims cover all such modifications and embodiments as fall within the true spirit and scope of the present invention.

What is claimed is:

1. A catheter for placement into a host comprising
   a flexible elongated body having a wall thickness sufficient to contain and transport fluid therein and having a forward end and tip for insertion into the host;
   a plurality of spaced apertures located in said forward end of said body spaced from said tip and positioned so as to minimize abrasion of tissue upon insertion of said catheter into said host; and
   said body having an internal bore having a non-circular cross section to increase the structural integrity and effective flow area of the catheter compared to those having a circular cross sectional bore;
   wherein each of said apertures extends through the wall thickness at an angle such that a portion of said wall thickness is visible when viewing said aperture perpendicular to the axis of said body.

2. The catheter of claim 1 wherein each of said apertures extends through said wall thickness at an angle of about 35° with respect to the longitudinal axis of said body.

3. The catheter of claim 1 wherein said apertures are aligned in rows which are spaced about 120° apart around the circumference of said body.

4. The catheter of claim 1 wherein the cross sectional area of the bore is a polygon, and wherein said apertures are positioned along the midpoint of each side of said polygon.

5. The catheter of claim 4 wherein an inner bore surface of said catheter is substantially smooth and free of any projections extending into said bore.

6. The catheter of claim 1 wherein said forward end of said body is integrally formed of a radioopaque material at least in the area surrounding said apertures to facilitate monitoring of the placement of said catheter within said host.

7. The catheter of claim 6 wherein said body further comprises means to indicate the depth of penetration of said catheter forward end.

8. The catheter of claim 7 wherein said means comprises markings of a radioopaque material to facilitate monitoring of the placement of said catheter.

9. A catheter for placement into the ventricular system of the brain of a subject comprising:
   a flexible elongated body having a wall thickness sufficient to contain and transport fluid therein and having a forward end and tip for insertion into the ventricular system of the brain of a subject; and
   a plurality of spaced apertures located in said forward end of said body spaced from said tip, each of said apertures extending through the wall thickness at an angle such that a portion of the wall thickness is visible when viewing said aperture perpendicular to the axis of said body so as to minimize abrasion of brain tissue upon insertion of said catheter and to hinder the growth of brain tissue into said catheter apertures thereby providing improved flow of fluid into or from said ventricular system;
   said body having internal bore of a polygonal cross-section to increase the structural integrity and effective flow area of the catheter compared to those having a circular cross-sectional bore.

10. The catheter of claim 9 wherein the cross-section of the bore is triangular, and wherein said apertures are positioned along the midpoint of each side of the triangle.

11. A method of accessing fluid within a host which comprises: providing a cateter comprising a flexible elongated body having a wall thickness sufficient to contain and transport fluid therein and having a forward end and tip for insertion into said host, and a plurality of spaced apertures located in said forward end of said body spaced from said tip, each of said apertures extending through the wall thickness at an angle such that a portion of said wall thickness is visible when viewing said aperture perpendicular to the axis of said body; inserting said catheter into said host while minimizing abrasion of tissue therein; and increasing the flow of fluid to or from said host by minimizing or preventing tissue growth into said catheter apertures through the position and configuration of said apertures in said catheter.

12. The method of claim 11 which further comprises selecting a catheter having a bore configured of a non-circular cross-section to increase the effective flow of fluid through the catheter and to increase the structural integrity of the catheter compared to those having a circular bore and further wherein the non-circular cross section is such that it prevents a flow restriction where said catheter is bent.

13. The method of claim 12 which further comprises providing the catheter with a bore said which is configured of a cross section having the form of an equilateral triangle and wherein said apertures are aligned in rows spaced about the circumference of said body at 120° intervals to coincide with the midpoint of each leg of said triangle.

14. The method of claim 11 which further comprises utilizing a stylet to assist in the insertion of said catheter in a manner such that the catheter is stretched so as to flatten said apertures to further reduce abrasion of tissue upon insertion therein.

15. The method of claim 11 wherein said catheter body further comprises means for indicating the depth of penetration of said catheter forward end and wherein said method further comprises inserting said catheter to a predetermined depth.

16. The method of claim 11 wherein said indicating means comprises radioopaque markings and wherein said method further comprises monitoring the placement of said catheter.

17. The method of claim 11 wherein cerebral spinal fluid in a ventrical within a human cranium is accessed by drilling an orifice in the cranium just anterior to a coronal suture in a midpupillary line of the cranium prior to inserting said catheter into said ventricle.

* * * * *